United States Patent [19]

Anderson et al.

[11] 4,260,633

[45] Apr. 7, 1981

[54] PESTICIDAL ESTERS OF AMINO ACIDS

[75] Inventors: Richard J. Anderson, Palo Alto, Calif.; Karen G. Adams, West Chester, Ohio; Clive A. Henrick, Palo Alto, Calif.

[73] Assignee: Zoecon Corporation, Palo Alto, Calif.

[21] Appl. No.: 142,522

[22] Filed: Apr. 21, 1980

[51] Int. Cl.³ .................. A01N 37/34; C07C 101/447; C07C 121/78
[52] U.S. Cl. ............................ 424/304; 260/453 AR; 260/465 D; 260/465 F; 562/456
[58] Field of Search .................. 260/465 D; 424/304; 562/456

[56] References Cited

U.S. PATENT DOCUMENTS

| 4,133,826 | 1/1979 | Warnant et al. | 260/465 D |
| 4,151,195 | 4/1979 | Warnant et al. | 260/465 D |
| 4,161,537 | 7/1979 | Katsuda et al. | 424/304 |
| 4,176,195 | 11/1979 | Stoutamire | 424/304 |
| 4,201,787 | 5/1980 | Katsuda et al. | 424/304 |

FOREIGN PATENT DOCUMENTS 2812169 10/1978 Fed. Rep. of Germany .

*Primary Examiner*—Dolph H. Torrence
*Attorney, Agent, or Firm*—Donald W. Erickson

[57] ABSTRACT

Novel diastereomeric esters of amino acids, novel intermediates therefor, synthesis thereof, and the use of said esters for the control of pests.

10 Claims, No Drawings

PESTICIDAL ESTERS OF AMINO ACIDS

This invention relates to novel diastereomeric esters of amino acids, novel intermediates therefor, synthesis thereof, and the use of said esters for the control of pests.

The esters of amino acids of the present invention are represented by the following generic formula (A):

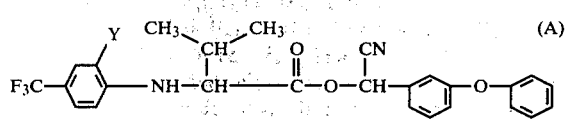

wherein,
Y is hydrogen or chloro; and
the acid is the R configuration and the alcohol is the S configuration or a mixture of the S configuration and the R configuration.

Certain esters of substituted-phenylamino acids have been described by Henrick & Garcia, Offenlegungsschrift 28 12 169, as being effective agents for the control of pests such as insects and acarids, acting in the manner of synthetic pyrethroids. The diastereomer and diastereomeric pair of formula (A) herein have been found to possess greatly improved pesticidal activity as compared to the racemic mixture or other diastereomeric pairs.

As a generally applicable method of synthesis, the compounds of formula (A) can be prepared by the reaction of an acid of formula (I), in its R configuration, with the S enantiomer or the R,S racemic mixture of α-cyano-3-phenoxybenzyl alcohol (II).

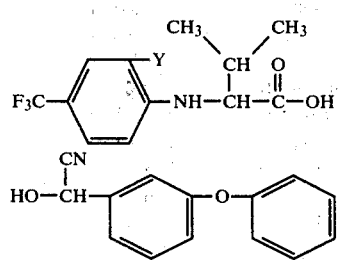

The above esterification can be carried out at a low temperature in the presence of 4-dimethylaminopyridine and dicyclohexylcarbodiimide.

The acid (I) is prepared from (R)-valine by conversion first to (R)-2-bromo-3-methylbutanoic acid and reaction of the latter with 4-trifluoromethylaniline to give the 4-substituted phenylamino acid. This can be chlorinated by use of N-chlorosuccinimide to prepare an acid of formula (I) wherein Y is chloro.

The R and the S enantiomers of the alcohol II are made by reacting racemic α-cyano-3-phenoxybenzyl alcohol with (R)-1-(1-naphthyl)ethyl isocyanate in the presence of 4,4-dimethylaminopyridine and a solvent such as toluene or benzene. The resulting carbamate is separated into its two diastereomers by liquid chromatography. The R,R isomer is further purified by crystallization and the R,S isomer, by repeated chromatography. Alternatively, the diastereomers can be separated from the mixture without initial chromatographic separation by adding a seed crystal of substantially optically pure (R,R)-carbamate and crystallizing out the R,R isomer. Each of the two separated diastereomers, in a solvent such as benzene, is reacted with trichlorosilane and triethylamine, at elevated temperature, to give the resulting R or S enantiomer of formula II.

In the prior art, synthetic pyrethroid esters containing the α-cyano-3-phenoxybenzyl alcohol moiety have been separated into their diastereomers after esterification, rather than by taking the desired acid enantiomer and the desired alcohol enantiomer and then esterifying them to make the diastereomer of the ester compound. Cf. Warnant et al., U.S. Pat. Nos. 4,133,826 & 4,151,195, and Stoutamire, U.S. Pat. No. 4,176,195. α-cyano-3-phenoxybenzyl alcohol is a labile molecule and stereoselective preparation or the resolution of the racemic alcohol has not previously been successful.

The compounds of the present invention of formula A are highly active pesticides, particularly against insects and acarids. The diastereomer and diastereomer pairs of the invention are unexpectedly more active than the racemic mixture or other diastereomeric pairs.

In the use of the compounds of formula A for combating insects and acarids for the protection of agricultural crops, for example soybeans, cotton, alfalfa, etc., a compound of formula A together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with pyrethroid synergists and/or other pesticides such as the carbamates, phosphates and insect growth regulators, e.g. propoxur, carbaryl, naled, dichlorvos, methoprene, kinoprene, hydroprene, cyhexatin and resmethrin.

Herein, and in the appended claims, the first letter designation refers to the configuration of the acid and the second letter designation refers to the configuration of the alcohol. For example, the diastereomer designated RS refers to $^R$acid $^S$alcohol.

The following examples are provided to illustrate the practice of the present invention. Temperature is given in degrees Centigrade. RT means room temperature.

EXAMPLE 1

To 12.4 g (75.5 mmol) of purified (R)-1-(1-naphthyl)-ethylamine in 130 ml of dry toluene is added, with stirring, gaseous hydrogen chloride for about 30 minutes, during which time an additional 100 ml of toluene is added to facilitate stirring. Phosgene is bubbled into the suspension, at RT, for about 20 minutes and then at reflux for 2 hours. Phosgene addition is stopped and the solution is heated at reflux for another 1.5 hours. The toluene is distilled off at atmospheric pressure and the residue is distilled (short path) at 0.30 mm to yield (R)-1-(1-naphthyl)ethyl isocyanate.

A solution of 11.0 g (56.0 mmol) of (R)-1-(1-naphthyl)-ethyl isocyanate, 12.6 g (56.0 mmol) of racemic α-cyano-3-phenoxybenzyl alcohol and 150 mg of 4-dimethylaminopyridine in 75 ml of toluene is heated at 50°, under nitrogen, for about 20 hours. The reaction mixture is cooled and poured into ether and 5% HCl. The organic phase is separated and washed with saturated sodium bicarbonate and with brine and is dried over sodium sulfate. Removal of solvent gives (R,S)-α-cyano-3-phenoxybenzyl (R)-N-1-(1-naphthyl)ethylcarbamate.

EXAMPLE 2

The (R,S)-α-cyano-3-phenoxybenzyl (R)-N-1-(1-naphthyl)-ethylcarbamate is purified by liquid chromatography on silica columns using ~23% ether/hexane. The first fraction, containing a high ratio of the faster eluting diastereomer, is collected and combined with several ml of ether. Hexane is added until crystals begin to form. This is allowed to crystallize overnight. The resulting crystals are collected and washed with hexane, giving (R)-α-cyano-3-phenoxybenzyl (R)-N-1-(1-naphthyl)ethylcarbamate, m.p. 121.5°–122°, specific rotation $[\alpha]_D^{25} = -15.2°$ (c = 10 mg/ml in CHCl$_3$), diastereomer purity = ~99%.

EXAMPLE 3

The second fraction obtained from purification of (R,S)-α-cyano-3-phenoxybenzyl (R)-N-1-(1-naphthyl)ethylcarbamate by liquid chromatography, from Example 2 above, which second fraction contains a high ratio of the slower eluting diastereomer, is collected. Since the slower eluting diastereomer does not readily crystallize out of solution, the fraction is further purified by liquid chromatography, using ether/hexane, and collection again of the second fraction. This purification process is continued until a substantially diastereomerically pure sample of the compound (S)-α-cyano-3-phenoxybenzyl (R)-N-1-(1=naphthyl)ethylcarbamate is obtained, m.p. 41°–41.5°, specific rotation $[\alpha]_D^{25} = -19.6°$ (c = 10 mg/ml in CHCl$_3$), diastereomer purity = ~98%.

EXAMPLE 4

To 1.99 g (4.7 mmol) of (R)-α-cyano-3-phenoxybenzyl (R)-N-1-(1-naphthyl)ethylcarbamate in 20 ml of benzene is added 725 μl (525 mg, 5.2 mmol) of triethylamine. The solution, under nitrogen, is stirred while 505 μl (675 mg, 5.0 mmol) of trichlorosilane is added. The reaction is warmed to 50° for 2.5 hours, and is then poured into saturated ammonium chloride and ether. The organic fraction is washed again with saturated ammonium chloride and then with brine (3×), and is dried over sodium sulfate overnight in the freezer. Solvent is removed by rotoevaporation, and the residue is washed repeatedly with hexane to remove the isocyanate. The urea contamination is removed by dissolving the product in ether/hexane (~1:1), and the solvent is then removed. Purification by thin layer chromatography (tlc) on silica gel plates developed in 30% ethylacetate/hexane yields the product, which is then dissolved in trichloromethane. The solvent is removed, giving (R)-α-cyano-3-phenoxybenzyl alcohol, specific rotation $[\alpha]_D = +15.2°$ (c = 10 mg/ml in acetone).

EXAMPLE 5

To a solution of 2.91 g (6.99 mmol) of (S)-α-cyano-3-phenoxybenzyl (R)-N-1-(1-naphthyl)ethylcarbamate in 30 ml of dry benzene under a nitrogen atmosphere is added 1.07 ml (0.78 g, 7.7 mmol) of triethylamine followed immediately by 0.75 ml (1.0 g, 7.4 mmol) of trichlorosilane. The reaction is heated at 50° for 3 hours and is then worked up and purified following the procedure of Example 4. The more polar band on the tlc plate is removed and extracted with trichloromethane to yield (S)-α-cyano-3-phenoxybenzyl alcohol, specific rotation $[\alpha]_D^{25} = -14.6°$ (c = 11 mg/ml in acetone).

EXAMPLE 6

To a solution of 20.0 g (170 mmol) of (R)-valine in 200 ml of 6 N hydrogen bromide, stirred under nitrogen in an ice bath, is added 18.0 g (260 mmol) of sodium nitrite portionwise over 1.5 hours, keeping the temperature below 8°. On completion of the addition, the reaction is stirred at 5° under nitrogen for about 5 hours and is then stored in the freezer overnight. Sodium chloride is added to saturate the solution and the mixture is then extracted with trichloromethane (3×). The combined organic extracts are washed with sodium bisulfite and with sodium chloride and dried over magnesium sulfate. Evaporation of the solvent under vacuum gives (R)-2-bromo-3-methylbutanoic acid, specific rotation $[\alpha]_D^{25} = +15.5°$ (c = 10% in methanol).

A solution of 10.01 g (55.3 mmol) of (R)-2-bromo-3-methylbutanoic acid in methanol is titrated with 1 M potassium hydroxide (~53 ml) in methanol to the phenolphthalein endpoint. The methanol is then removed under high vacuum at 35°, and the solid is kept at 35° under high vacuum for one hour. 4-Trifluoromethylaniline (23.89 g, 148.3 mmol) is added to the salt, and the mixture is heated in a pre-heated oil bath (90°) under nitrogen for 30 minutes. The mixture is then cooled and worked up immediately by partitioning between pentane/5% sodium hydroxide. The layers are separated and the pentane phase is extracted with 5% sodium hydroxide (2×). The combined aqueous phases are extracted with pentane (2×) and acidified with cold conc. hydrochloric acid. The aqueous phase is then extracted with ether (3×), and the combined ether phases are washed with brine and dried over magnesium sulfate. Filtration and evaporation yield (R)-2-(4-trifluoromethylphenylamino)-3-methylbutanoic acid.

To 35 ml of carbon tetrachloride are added 2.81 g (10.0 mmol) of (R)-2-(4-trifluoromethylphenylamino)-3-methylbutanoic acid and 1.33 g (9.96 mmol) of N-chlorosuccinimide, and the mixture is heated to reflux for 1 hour. The mixture is worked up by partition between ether/water. The layers are separated and the aqueous phase is extracted with ether (2×). The combined organic extracts are washed with water and with brine, dried over magnesium sulfate, filtered and evaporated, giving (R)-2-(2-chloro-4-trifluoromethylphenylamino)-3-methylbutanoic acid.

EXAMPLE 7

(S)-2-bromo-3-methylbutanoic acid is prepared following the procedure of Example 6 from (S)-valine and sodium nitrite and 6 N hydrogen bromide. Specific rotation of the bromo acid is $[\alpha]_D^{25} = -17.2°$ (c=10% in methanol).

1.5 Grams (8.3 mmol) of the (S)-2-bromo-3-methylbutanoic acid is titrated with 8 ml of 1 M potassium hydroxide in methanol to a phenolphthalein endpoint. The solution is evaporated under high vacuum at 40° for 1 hour, and 0.51 g (2.33 mmol) of the resulting salt is heated together with 1.52 g (9.43 mmol) of 4-trifluoromethylaniline at 90°-95° under nitrogen for 1 hour. Heating is discontinued and the reaction worked up immediately by partition between ether/5% sodium hydroxide. The layers are separated and the organic phase is extracted with 5% sodium hydroxide (2×). The aqueous layers are combined and washed with ether (2×), then acidified with ice and conc. HCl and extracted with ether (3×). The latter ether extracts are washed with brine, dried over magnesium sulfate, filtered and evaporated, giving (S)-2-(4-trifluoromethylphenylamino)-3-methylbutanoic acid.

Following the method of Example 6, (S)-2-(4-trifluoromethylphenylamino)-3-methylbutanoic acid and N-chlorosuccinimide in carbon tetrachloride are reacted, yielding (S)-2-(2-chloro-4-trifluoromethylphenylamino)-3-methylbutanoic acid.

EXAMPLE 8

Into 4.5 ml of methylene chloride containing 22.5 mg of 4-dimethylaminopyridine are added 439 mg (1.48 mmol) of (R)-2-(2-chloro-4-trifluoromethylphenylamino)-3-methylbutanoic acid and 329 mg (1.46 mmol) of (S)-α-cyano-3-phenoxybenzyl alcohol. The solution is cooled in an ice bath and 380 mg (1.82 mmol) of dicyclohexylcarbodiimide is added. The mixture is stirred at 0° for 1 hour and is then worked up by partition between ether/hexane. The aqueous phase is extracted with ether, and the ether extract is washed with water (2×) and brine, dried over magnesium sulfate, filtered and evaporated. The product is purified by radial thin layer chromatography (2 mm silica gel rotor eluting with 12% ether/hexane). Higher diastereomeric purity is obtained by further radial tlc, yielding the final product (S)-α-cyano-3-phenoxybenzyl (R)-2-(2-chloro-4-trifluoromethylphenylamino)-3-methylbutanoate, specific rotation = +46.3° (in CHCl$_3$), diastereomer purity = ~98%.

EXAMPLE 9

(R)-2-(2-chloro-4-trifluoromethylphenylamino)-3-methylbutanoic acid (0.20 g, 0.68 mmol), racemic α-cyano-3-phenoxybenzyl alcohol (0.17 g, 0.75 mmol) and dimethylaminopyridine (10 mg, 0.08 mmol) are placed in 2 ml methylene chloride/2 ml dimethylformamide. The mixture is cooled in an ice bath under nitrogen and 0.16 g (0.77 mmol) of dicyclohexylcarbodiimide is added. The mixture is kept cold, with stirring, for 2 hours.

The mixture is filtered and the solid is washed several times with ether. The ether is then extracted with water and the layers are separated. The aqueous phase is extracted with ether (2×), and the combined ether extracts are washed with dilute HCl and with brine, dried over magnesium sulfate, filtered and evaporated. Purification by preparative thin layer chromatography eluting with 10% ether/hexane gives a product composed primarily of the diastereomer pair consisting of (S)-α-cyano-3-phenoxybenzyl (R)-2-(2-chloro-4-trifluoromethylphenylamino)-3-methylbutanoate (42%) and (R)-α-cyano-3-phenoxybenzyl (R)-2-(2-chloro-4-trifluoromethylphenylamino)-3-methylbutanoate (52%).

EXAMPLE 10

Approximately 0.5 g of the compound (R,S)-α-cyano-3-phenoxybenzyl (R)-N-1-(1-naphthyl)ethylcarbamate from Example 1 is dissolved in ~1 ml of ether and a few drops of hexane are added. To this is added a seed crystal of ~99% optically pure (R)-α-cyano-3-phenoxybenzyl (R)-N-1-(1-naphthyl)ethylcarbamate from Example 2, and the mixture is allowed to crystallize overnight. The solid is separated out and washed with hexane several times. The solid shows a diastereomer purity of 72% (R)-α-cyano-3-phenoxybenzyl (R)-N-1-(1-naphthyl)ethylcarbamate. Several additional crystallizations of this solid gives compound of 98% diastereomeric purity.

The separated mother liquor is purified by liquid chromatography as in Example 3 to give (S)-α-cyano-3-phenoxybenzyl (R)-N-1-(1-naphthyl)carbamate.

EXAMPLE 11

Following the procedure of Example 8, (R)-2-(4-trifluoromethylphenylamino)-3-methylbutanoic acid and (S)-α-cyano-3-phenoxybenzyl alcohol are combined, in the presence of 4-dimethylaminopyridine and dicyclohexylcarbodiimide, to yield (S)-α-cyano-3-phenoxybenzyl (R)-2-(4-trifluoromethylphenylamino)-3-methylbutanoate, specific rotation = +62.1° (c=9 mg/ml in CHCl$_3$).

EXAMPLE 12

Comparative activity of the four diastereomers of α-cyano-3-phenoxybenzyl 2-(2-chloro-4trifluoromethylphenylamino)-3-methylbutanoate and of the prior art diastereomeric mixture of the compound was determined by testing for toxicity on insect pests.

A. Two groups of 10 each of 0-24 hr III instar *Heliothis virescens* larvae were treated with 1 μl of the test compound in acetone at different dosage rates by application to the dorsum of the thorax. Two groups of 10 each were treated identically with 1 μl acetone as controls. Larvae are held individually in 30 ml plastic cups provided with artificial medium for 72 hours at 25° and 16 hr photoperiod. After 72 hr the number of dead is calculated as a percentage of the total number originally treated and then corrected for any mortality in the control group using Abbott's formula. The toxicity is expressed as LD$_{50}$, which is the dosage, in μg per insect, required to kill 50% of the test insects. The results are presented in Table I.

B. Fifteen 72-hr-old adult female *Musca domestica* L. are anesthetized with ether vapor. These are then treated with 1 μl of the test compound diluted to different dosage rates in acetone applied to the dorsal surface of the prothorax. They are held in an assay container with milk-saturated cotton at 25°, 16 hr photoperiod for 24 hours. The effect is stated as the number dead calculated as a percentage of the total, corrected for any control mortality using Abbott's formula. The toxicities of the compounds, expressed as LD$_{50}$, are presented in Table 1 below.

TABLE I

ACTIVITY OF α-CYANO-3-PHENOXYBENZYL 2-(2-CHLORO-4-TRIFLUOROMETHYLPHENYLAMINO)-3-METHYLBUTANOATE COMPOUNDS, AS LD$_{50}$ (μg/INSECT)

| Compound | Diastereomer | H. virescens | M. domestica |
|---|---|---|---|
| A | RR | 0.320 | 2.180 |
| B | SR | 91.000 | 29.900 |
| C | SS | >100 | 39.900 |
| D | RS | 0.0181 | 0.0378 |
| E | RS,SR,RR,SS | 0.0803 | 0.156 |

The results of the above tests show that compound D, (S)-α-cyano-3-phenoxybenzyl (R)-2-(2-chloro-4-trifluoromethylphenylamino)-3-methylbutanoate, is more than four times as active as the diastereomeric mixture (R,S)-α-cyano-3-phenoxybenzyl (R,S)-2-(2-chloro-4-trifluoromethylphenylamino)-3-methylbutanoate (compound E). The three other diastereomers are all much less active than the diastereomeric mixture (compound E).

EXAMPLE 13

Following the methods described in Example 12, comparative activity of the four diastereomers and the diastereomeric mixture of α-cyano-3-phenoxybenzyl 2-(4-trifluoromethylphenylamino)-3-methylbutanoate against III instar *Heliothis virescens* larvae and against adult female *Musca domestica* was determined. The results are presented in Table II.

TABLE II

ACTIVITY OF α-CYANO-3-PHENOXYBENZYL 2-(4-TRIFLUOROMETHYLPHENYLAMINO)-3-METHYLBUTANOATE COMPOUNDS, AS LD$_{50}$ (μg/INSECT)

| Compound | Diastereomer | H. virescens | M. domestica |
|---|---|---|---|
| F | RR | 0.53 | 0.82 |
| G | SR | >100 | 2.28 |
| H | SS | 2.53 | 0.17 |
| J | RS | 0.018 | 0.033 |
| K | RS,SR,RR,SS | 0.055 | 0.084 |

Compound J, (S)-α-cyano-3-phenoxybenzyl (R)-2-(4-trifluoromethylphenylamino)-3-methylbutanoate, is three times as active as the diastereomeric mixture (R,S)-α-cyano-3-phenoxybenzyl (R,S)-2-(4-trifluoromethylphenylamino)-3-methylbutanoate (compound K) on Heliothis and more than 2.5 times as active on Musca. The other three diastereomers have much lower activity.

What is claimed is:

1. A compound of the following formula A:

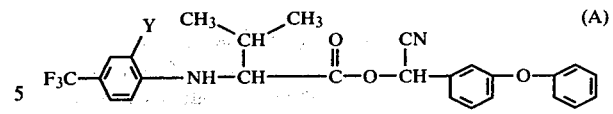

wherein,
Y is hydrogen or chloro; and
the acid is the R configuration and the alcohol is the S configuration or a mixture of the S configuration and the R configuration.

2. The diastereomer (S)-α-cyano-3-phenoxybenzyl (R)-2-(2-chloro-4-trifluoromethylphenylamino)-3-methylbutanoate, according to claim 1.

3. The diastereomeric pair consisting of (S)-α-cyano-3-phenoxybenzyl (R)-2-(2-chloro-4-trifluoromethylphenylamino)-3-methylbutanoate and (R)-α-cyano-3-phenoxybenzyl (R)-2-(2-chloro-4-trifluoromethylphenylamino)-3-methylbutanoate, according to claim 1.

4. The diastereomer (S)-α-cyano-3-phenoxybenzyl (R)-2-(4-trifluoromethylphenylamino)-3-methylbutanoate, according to claim 1.

5. The diastereomeric pair consisting of (S)-α-cyano-3-phenoxybenzyl (R)-2-(4-trifluoromethylphenylamino)-3-methylbutanoate and (R)-α-cyano-3-phenoxybenzyl (R)-2-(4-trifluoromethylphenylamino)-3-methylbutanoate, according to claim 1.

6. A method for controlling insects or acarids which comprises applying to said insect or acarid or their habitat a pesticidally effective amount of a compound of claim 1.

7. The method according to claim 6 wherein the compound is (S)-α-cyano-3-phenoxybenzyl (R)-2-(2-chloro-4-trifluoromethylphenylamino)-3-methylbutanoate.

8. The method according to claim 6 wherein the compound is the diastereomeric pair consisting of (S)-α-cyano-3-phenoxybenzyl (R)-2-(2-chloro-4-trifluoromethylphenylamino)-3-methylbutanoate and (R)-α-cyano-3-phenoxybenzyl (R)-2-(2-chloro-4-trifluoromethylphenylamino)-3-methylbutanoate.

9. The method according to claim 6 wherein the compound is (S)-α-cyano-3-phenoxybenzyl (R)-2-(4-trifluoromethylphenylamino)-3-methylbutanoate.

10. The R enantiomer of an acid of the following formula:

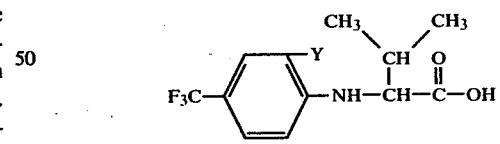

wherein Y is hydrogen or chloro.

* * * * *